United States Patent
Cannon

(10) Patent No.: US 11,213,222 B2
(45) Date of Patent: Jan. 4, 2022

(54) METHOD AND SYSTEM FOR DETERMINING RESIDUAL LUNG VOLUME

(71) Applicant: Sterling L Cannon, Midland, GA (US)

(72) Inventor: Sterling L Cannon, Midland, GA (US)

(73) Assignee: PhysicsIP, Inc., Midland, GA (US)

( * ) Notice: Subject to any disclaimer, the term of this patent is extended or adjusted under 35 U.S.C. 154(b) by 533 days.

(21) Appl. No.: 16/168,645

(22) Filed: Oct. 23, 2018

(65) Prior Publication Data

US 2019/0104966 A1 Apr. 11, 2019

Related U.S. Application Data

(63) Continuation-in-part of application No. 16/027,246, filed on Jul. 3, 2018.

(60) Provisional application No. 62/570,570, filed on Oct. 10, 2017.

(51) Int. Cl.
| | |
|---|---|
| *A61B 5/091* | (2006.01) |
| *A61M 16/00* | (2006.01) |
| *A61B 5/087* | (2006.01) |
| *A61B 5/097* | (2006.01) |
| *A61B 5/08* | (2006.01) |

(52) U.S. Cl.
CPC .......... *A61B 5/091* (2013.01); *A61M 16/024* (2017.08); *A61B 5/0803* (2013.01); *A61B 5/087* (2013.01); *A61B 5/097* (2013.01); *A61M 2016/0027* (2013.01)

(58) Field of Classification Search
None
See application file for complete search history.

(56) References Cited

U.S. PATENT DOCUMENTS

| | | | | |
|---|---|---|---|---|
| 3,810,461 | A * | 5/1974 | McCormick | A61B 5/093 600/541 |
| 3,848,583 | A * | 11/1974 | Parr | A61B 5/0871 600/541 |
| 4,873,866 | A * | 10/1989 | Fairbanks | G01N 9/10 73/437 |
| 2006/0176686 | A1* | 8/2006 | McVicker | F21S 9/022 362/183 |
| 2014/0323836 | A1* | 10/2014 | Kusukame | A61B 5/6891 600/344 |

(Continued)

OTHER PUBLICATIONS

Wilmore, Jack H., and Albert R. Behnke. "An anthropometric estimation of body density and lean body weight in young men." Journal of Applied Physiology 27.1 (1969): 25-31. (Year: 1969).*

(Continued)

*Primary Examiner* — Jacqueline Cheng
*Assistant Examiner* — Jairo H Portillo
(74) *Attorney, Agent, or Firm* — Steven C. Stewart

(57) ABSTRACT

A method and apparatus to determine residual long volume of a subject is disclosed. Physical characteristics of water in a pool and surrounding air barometric pressure is determined. A body of the subject is completely submerged in the pool of water at a known depth and exhales. The subject then moves to a shallower depth in the water and completely exhales air into an air measuring device. The residual lung volume is then determined and displayed based on the water characteristics, barometric air pressure, the amount of air exhaled into the air measuring device, and the depths of the subject during exhalation.

10 Claims, 7 Drawing Sheets

(56) References Cited

U.S. PATENT DOCUMENTS

2016/0287139 A1* 10/2016 Luttrell ............. A61M 16/0051
2018/0000379 A1* 1/2018 Eltorai ................ A61B 5/7475

OTHER PUBLICATIONS

Warner, J. G., et al. "A hydrostatic weighing method using total lung capacity and a small tank." British journal of sports medicine 20.1 (1986): 17-21. (Year: 1986).*

Delisio, Mary J. Comparison of hydrostatic weighing at residual volume and total lung capacity in boys. Diss. 1982. (Year: 1982).*

Luft, U. C., and T. P. K. Lim. "Modified Procedure for the determination of body volume by hydrostatic weighing." Techniques for Measuring Body Composition. National Academy of Sciences, National Research Council, Washington, DC (1961): 107. (Year: 1961).*

Patterson, P. E., and Matthew Distel. "Development of an underwater weighing system for determining body composition." Biomedical Sciences Instrumentation 34 (1997): 363-367. (Year: 1997).*

* cited by examiner

METHOD AND SYSTEM FOR DETERMINING RESIDUAL LUNG VOLUME

RELATED APPLICATION

This application is a continuation in part of U.S. patent application Ser. No. 16/027,246, filed Jul. 3, 2018, titled "Method and System for Determining Body Composition", which claims the benefit of U.S. provisional application No. 62/570,570, file Oct. 10, 2017, the contents of both applications are hereby incorporated by reference.

TECHNICAL FIELD

These claimed embodiments relate to a method and system for determining Residual Lung Volume (the amount of air left in the lungs after a maximum exhalation) and more particularly to determining Residual Lung Volume based on a volume of exhalation of a subject at known water depths.

BACKGROUND OF THE INVENTION

A method and apparatus for determining Residual Lung Volume is disclosed.

Exemplary processes to determine accurate Residual Lung Volume require either a skilled respiratory therapist working with either compressed pure gasses and sensitive equipment that measure lung gas concentrations, or require the skilled respiratory therapist working with a large airtight rigid structure of known volume and very sensitive air pressure monitoring equipment. These processes to determine accurate lung volumes can be an expensive and time-consuming.

SUMMARY OF THE INVENTION

In one implementation, a method is disclosed for determining Residual Lung Volume of a subject. The method includes determining with air pressure measurement device ambient air pressure and determining with a water density measurement device water density of water in a pool. The subject is submerged in a pool of water at a first depth and completely exhaling air into the pool at the first depth. The subject is moved to a shallower second depth and completely exhaling air into air volume measuring device used to measure a volume of air exhaled by the subject as the body of the subject is submerged below the surface of the water at the second depth. A lung volume computing device receives a) the determined ambient air pressure from the air pressure measurement device, b) the determined water density measurement device water density of water in the pool, c) the first and second depth, and d) the volume of air exhaled by the subject as measured with the air measuring device. The lung volume computing device determines a residual lung volume (V1) of the subject based on the received a) determined ambient air pressure, b) the determined water density, c) the first and second depth, and d) a measured volume of air exhaled by the subject into the air volume measuring device (MVOA).

In another implementation, a system for determining residual lung capacity of a subject is disclosed. The system includes an air pressure measurement device to determine ambient air pressure, a water density measurement device to determine water density of water in a pool, and an air volume measuring device (AVMD) that includes a transparent bag with an open end and a closed end, the bag having a length extending longer than a width. The bag includes equally spaced radial demarcations imprinted on the bag and extending from the closed end to the open end around an axis extending through the length of the bag, a plurality of numbers respectively corresponding to a lung volume used to determine a residual lung volume of the subject when the subject exhales air into the bag when an entire body of the subject is submerged below a surface of the pool of water at a second shallow depth after the subject completely exhales air at a first deeper depth in the pool. A lung volume computing device is provided that includes circuitry to receive a) the determined ambient air pressure from the air pressure measurement device, b) the determined water density measurement device water density of water in the pool, c) a measurement corresponding to the first and second depth, and d) a measured volume of air exhaled by the subject as measured with the AVMD. The lung volume computing device also includes circuitry to determine a residual lung volume (V1) of the subject based on the received a) determined ambient air pressure, b) the determined water density, c) the measurement of the first and the second depth, and d) a measured volume of air exhaled by the subject into the AVMD.

This method for determining residual lung volume of the subject may be useful for determining the subject's body fat percent while performing underwater weighing. This method is an improvement because the subject's residual lung volume varies based on posture and the position of the lungs relative to the mouth while underwater. (There is a larger residual volume compared to spirometry derived RV when the mouth is lowered in relation to the lungs, given the increased pressure required to expel the air from the lungs at a greater pressure. There also is a lower residual volume compared to RV measured in air when the mouth is higher than the lungs underwater due to pressure exerted on the diaphragm via the abdominal cavity). This method allows you to measure your residual volume underwater in whatever position you will be in while performing the full exhale for underwater weighing (hydrostatic body composition testing)

BRIEF DESCRIPTION OF THE DRAWINGS

The detailed description is described with reference to the accompanying figures. In the figures, the left-most digit(s) of a reference number identifies the figure in which the reference number first appears. The use of the same reference number in different figures indicates similar or identical items.

DETAILED DESCRIPTION

Figure 1A:
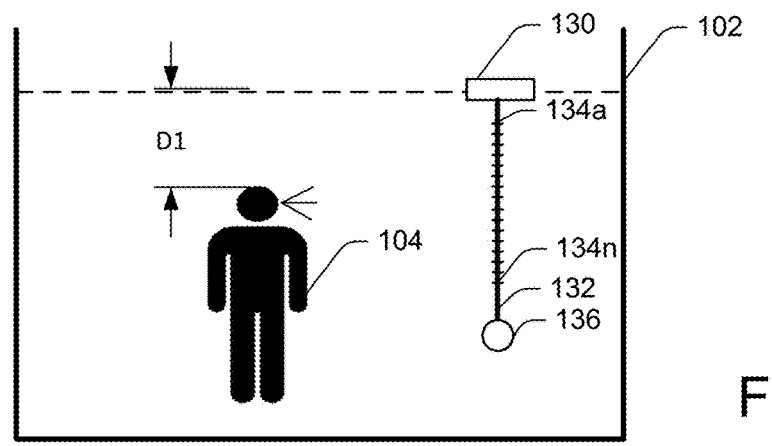
FIG. 1A is a diagram of a subject in water and exhaling at a first known depth.

Referring to FIG. 1A, there is shown a pool 102 of water in which a subject 104 is submerged to a depth D1. The subject 104, completely exhales a normal breath and moves to a shallower depth D2 as shown in FIG. 1B.

Figure 1B:
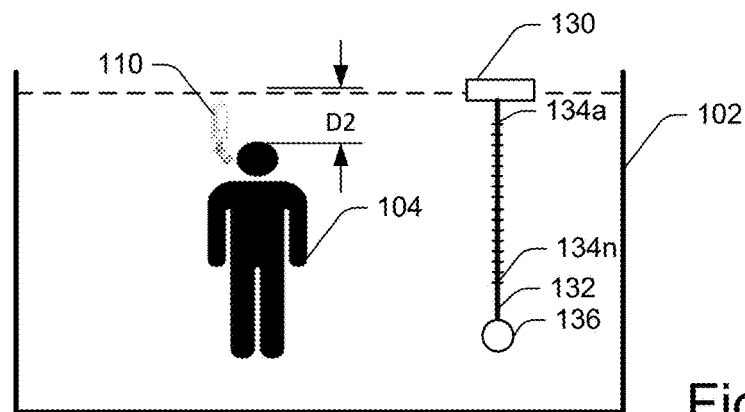
FIG. 1B is a diagram of a subject in water and exhaling at a second known depth into a container.

Referring to FIG. 1B, the subject after moving to shallower depth D2 (where D2 is less than D1) in pool 102, completely exhales a breath into an open end of container 110 (also referred to herein as a "air volume measuring device") and manually seal the bottom/open end of the container 110. In one implementation, the container 110 is constructed from flexible transparent plastic, and is open at one end and sealed at its other end. In one implementation, container 110 is sealed at one end using a connected a mouth piece and tube 114 in which the subject breaths through when exhaling. Exemplary container 110 is shown and described in more detail in connection with FIGS. 1C and 5. The container 110 may have line markings and numerical markings at regular equally spaced intervals from the open end of the container 110 to the closed end of the container 110 so that a container's volume of air may be easily determined. In another implementation, container 110 may be constructed from a ridged material.

Figure 1C:
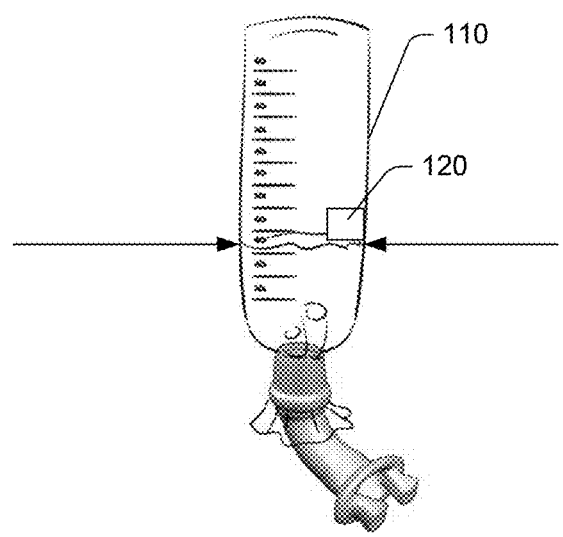
FIG. 1C is a diagram illustrating identifying the volume of exhaled air the container in FIG. 1B.

Referring to FIG. 1C, one the subject 104 exhales into the container 110, the container 110 could be raised above the surface of the water in pool 102. The bottom of the container 110 could then be squeezed so that only a small amount of water would remain in the container, and the air exhaled by the subject would completely fill and expand the portion of the container not including the water. In one implementation, a device, such as a floating barometric sensor 120, could be placed in the container 110 to provide a visual indication, such as a green light, when the container 110 reaches at predetermined inflation pressure. The density of water could be measured with a hydrometer or calculated based on pool 102 water purity and water temperature.

When the container 110 is at the predetermined inflation pressure, the number on the marking viewable in the air-filled expanded portion of the container 110 just above the surface of water in the container could then be determined. The determined number of the marking would be provided along with a water temperature for measurement in distilled or pure water or a direct water density measurement from a hydrometer or similar apparatus, the depth D1 and the depth D2 to computing device 208 (See FIG. 2) to compute the residual lung volume of subject 104 using the method described in FIG. 4. The beginning depth D1 and ending depth D2 could be estimated by the depth of the pool 102 or directly measured and converted to meters.

Although a collapsible (bag) container 110 is shown, a rigid volumetric container or an electronic volume detector may be used to collect and measure the volume of air exhaled by the subject.

Referring to FIGS. 1A and 1B, a float 130 may be provided in pool 102 connected to rope 132 at one end. Optionally at the other end or rope 132 may be a weight 136. Markings 134a-134n may be equally spaced and placed along rope 132 to indicate a depth in pool, such as D1 and D2. Numbers (not shown) may be placed adjacent markings 134a-134n to indicate a water depth. The subject 104 observes the number adjacent markings 134a-134n on rope 132 at depth D1 and D2 (or submerges into pool 102 to depth D1 and D2 as indicated by the numbers adjacent one or more markings 134a-134n) respectively before exhaling.

Figure 2:
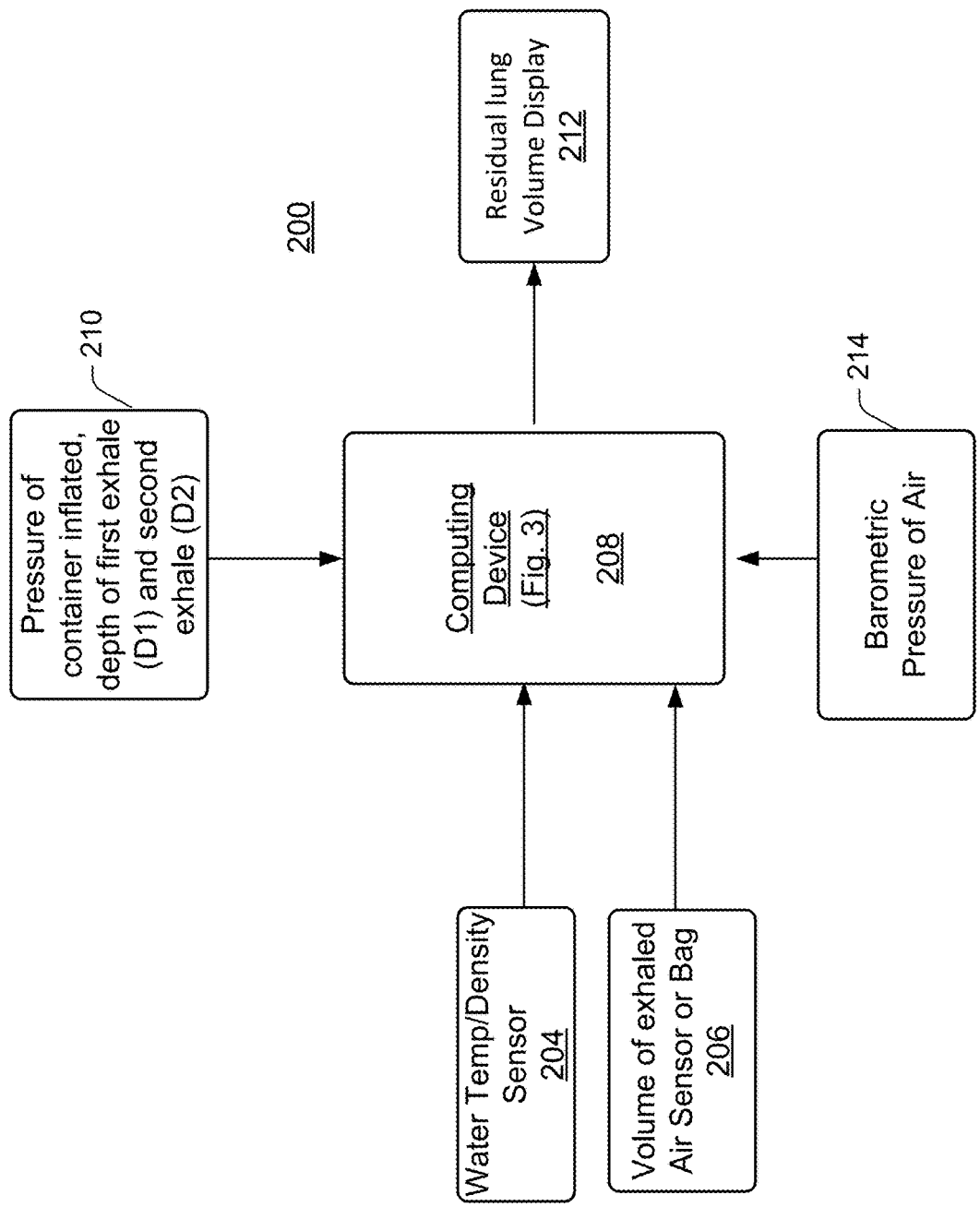
FIG. 2 is a simplified schematic diagram of a system for calculating residual lung volume.

Referring to FIG. 2, there is shown a system 200 for calculating residual lung volume of a subject. System 200 includes water temperature sensor or water density measuring device 204, a barometric pressure measuring device 214 (that can be used to measure ambient air pressure), and an input device 206 to receive information from a volume sensor, such as Bag/Container 110 (FIG. 1C) having numerical markings that indicates a volume of exhaled air by subject, an input device 210 (such as a keyboard, voice detector or other input device) to receive pressure of container inflated indicator, depth D1 and D2, and a residual lung volume display device 212, all coupled to Computing Device 208 (also referred to herein as "a lung volume computer device").

Water temperature/density 204 sensor may include a thermometer that measure the temperature of the water, a hydrometer that measure the density of water in the pool 102 and/or and may include a device to measure total dissolved solids in the water. Sensor 206 may be a regulator connected to a sensor that detects an amount of air exhaled by subject. This affects the water density for a given temperature exhaled by the subject. Water density may be measured directly as well with a hydrometer or similar device. An exemplary sensor 206 may include container 110.

In one implementation sensors 204-210, and 214 send signals to computing device 208 via an electronics network, via a Bluetooth transmitter, or via a telecommunication line. In another implementation sensors 202-210, and 214 provide a LED/LCD display 212 that can be read by a user. Pressure of an inflated container, the depth D1 and D2 can be entered manually via an input device 210. Input device 210 may include a keyboard or other input output device for manual entry of data into computing device 208.

The computing device 208 could transmit an indication of residual lung volume (request for inputs or any other measurement/calculation determined by computing device 208) to display/output device 212.

Figure 3:
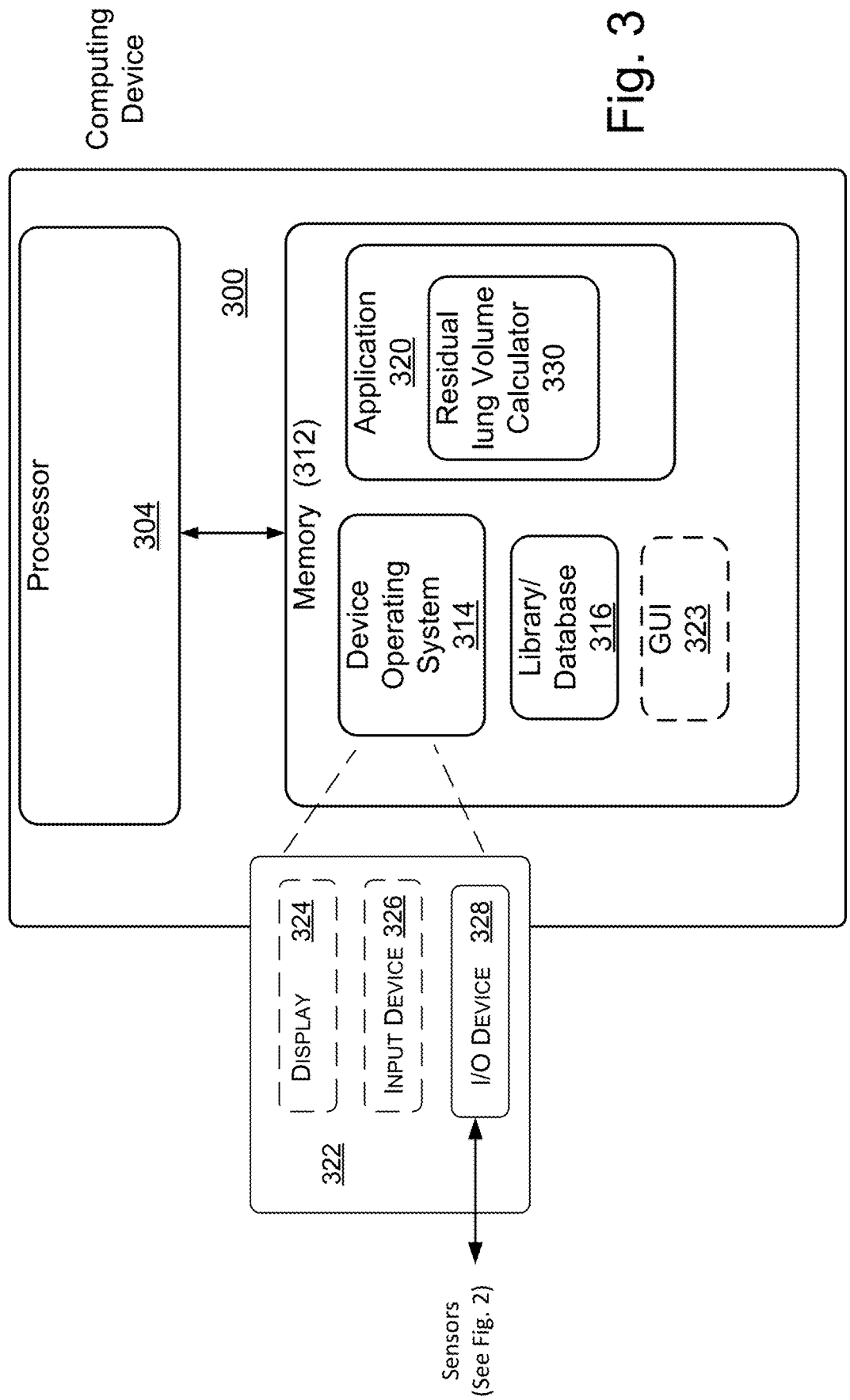
FIG. 3 is a simplified schematic diagram of the computing device shown in FIG. 2.

Referring to FIG. 3, there are illustrated selected modules in computing device 300 (computing device 208 of FIG. 2). Computing device 300 includes a processing device 304, memory 312, and display/input device 322. Processing device 304 may include a microprocessor, microcontroller or any such device for accessing memory 312 and display/input device 322. Processing device 304 has processing capabilities and memory suitable to store and execute computer-executable instructions. In one example, processing device 304 includes one or more processors.

Processing device 304 executes instructions stored in memory 312, and in response thereto, processes signals from and display/input device 322. Device 322 may include input device 326, network i/o device 328 that includes network and communication circuitry for communicating with a communications network (FIG. 2) and output device 329 for communicating with a printer. Input device 326 (device 210 in FIG. 2) receives inputs from a user of the personal computing device and may include a keyboard, mouse, track pad, microphone, audio input device, video input device, or touch screen display. Display device 324 (device 212 in FIG. 2) may include an LED, LCD, CRT or any type of display screen.

Memory 312 may include a non-transitory volatile and nonvolatile memory, removable and non-removable media implemented in any method or technology for storage of information, such as computer-readable instructions, data structures, program modules or other data. Such memory includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, RAID storage systems, or any other medium (including a non-transitory computer readable storage medium) which can be used to store the desired information, and which can be accessed by a computer system.

Modules stored in memory 312 of the computing device 208 may include an operating system 314, an I/O controller 312, a library 316, an application 320 and a graphical user interface 323. Operating system 314 may be used by application 320 to operate Display 324. Library 316 may include preconfigured parameters (or set by the user before or after initial operation) such as computing device operating parameters and configurations. Application 320 may include a residual lung volume calculator 330 and other code for executing the processes shown or describe in connection with FIGS. 1-2, and FIG. 4.

Figure 4:
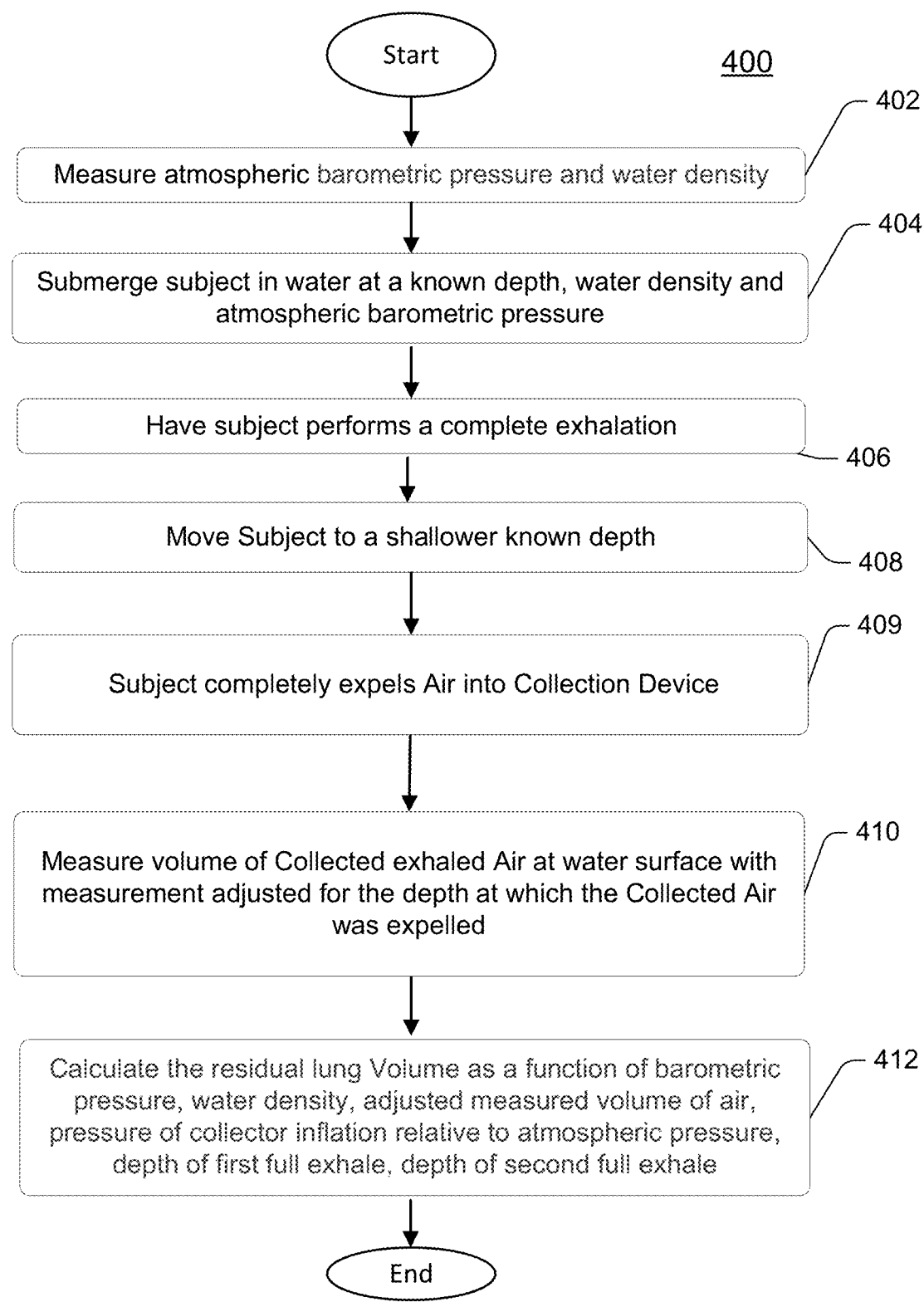
FIG. 4 is a flow chart of the process for determining Residual Lung Volume with the system shown in FIG. 2.

Illustrated in FIG. 4, there is shown a process 400 for determining body composition. The exemplary process in FIG. 4 is illustrated as a collection of blocks in a logical flow diagram, which represents a sequence of operations that can be implemented in hardware, software, and a combination thereof. In the context of software, the blocks represent computer-executable instructions that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the process. For discussion purposes, the processes are described with reference to FIG. 4, although it may be implemented in other system architectures.

Referring to FIG. 4, a process 400 is shown for determining residual lung capacity of a subject using the processor and modules shown in FIG. 3.

In the process 400, the atmospheric barometric pressure is measured, and a density of water in a pool is determined using conventional tools (which may involve sensors that determine water temperature and composition). The density of the water can be measured directly rather than being computed from temperature and estimate of dissolved solids measured from an EC meter. These measurements and determinations entered via Input/output device 210 to computing device 208 (FIG. 2) in block 402.

In block 404, the enters a pool of water 102 and is submerged at a known relatively deep depth (D1), with the given measured water density and atmospheric pressure (in block 402). The depth D1 is then transferred to computing device 208 (FIG. 2).

In block 406, the subject performs a complete exhalation into the pool.

In block 408, the subject is moved to a shallower known depth D2 and in block 409 completely exhales their breath via a tube into container 110. The volume of air exhaled by the subject to maximum exhalation is collected in the container 110.

Alternately, an electronic breath measuring/recording device senses is used in place of container, which transmits to the computing device the amount of the volume of air exhaled by the subject. Examples of electronic measuring devices include EasyOne® Air spirometer made by ndd Medical Technologies, Inc. company of Andover, Mass.

If In block 410, the container 110 is placed in an upright position, closed at its open end and squeezed so that the air fills up the container. The open end is squeezed so that pressure is increased on the inside of the container 110 until a floating barometric sensor 120 (FIG. 1C) indicates when the correct inflation pressure is reached by displaying a green light. The volume of collected exhaled air at water surface is measured and adjusted for the depth at which the collected air was expelled. The marking on the container 110 at the level of the surface of water in the bag is read and inputted into computing device using input output device 216. This measurement may be used to calculate actual volume of lung exhalation by adjusting for measured container characteristics, barometric pressure and distance underwater D2 at which the pressure and markings are measured.

In block 412, the residual lung volume is calculated by computing device 208 as a function of barometric pressure, water density (WD), adjusted measured volume of air, pressure of collector inflation relative to atmospheric pressure, depth D1 of the first full exhale, depth of second full exhale D2. The lung volume computing device determines a residual lung volume (V1) of the subject based on the received a) determined ambient air pressure, b) the determined water density, c) the first depth D1 and second depth D2, and d) a measured volume of air exhaled by the subject into the air volume measuring device (MVOA).

The water density measurement device determines density of water (WD) in the pool by measuring a water temperature and a water purity. Specifically, the density of water (WD) may be computed as follows: WD=Density for a given concentration of salt in weight % (C)=(750.2834+ 26.7822*C+−0.26389*$C^2$)+(1.90165+−0.11734*C+ 0.00175*$C^2$)*T+(−0.003604+0.0001701*C+− 0.00000261*$C^2$)*$T^2$). The calculation for density of water with NaCl is good for salt water swimming pools and could incorporate another input device to measure the Total Dissolved Solids (TDS). One such device to measure the Total Dissolved solids is a TDS Water Tester marketed under the brand name of PATEA™ by Ye Shun cai of Huanggang Town, Raoping Count No. 5 Shanxiading Fengwei Guangdong CHINA.

In one implementation, residual lung volume V1 is determined with lung volume computing device 208 using the formula V1=P2*MVOA/(P1−P2), where P1 is an underwater pressure determined based on the first depth D1 and the water density (WD), and P2 is an underwater pressure determined at the second depth. For Depth D1, the pressure is the barometric pressure in pascals plus the product of the density of the water, the depth of D1, and the acceleration of gravity. Pressure P2 is determined based on the second depth D2 and the water density. For Depth D2, the pressure is the barometric pressure in pascals plus the product of the density of the water, the depth of D2, and the acceleration of gravity.

Computing device 208 may then send the determined residual lung volume to indicator 212 for display.

Figure 5:
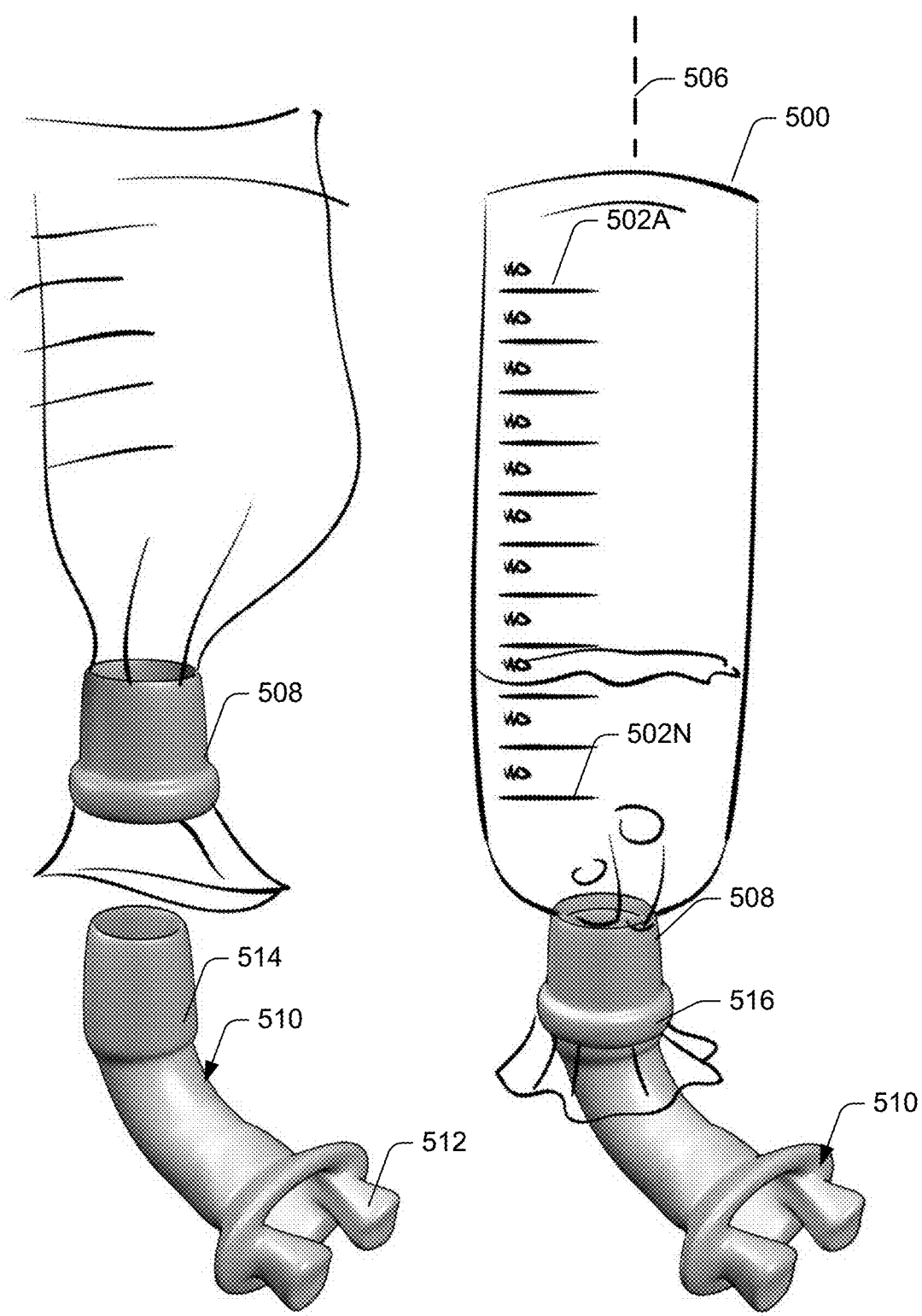
FIG. 5 is isometric diagram of an exemplary container with a mouth piece as shown in FIGS. 1B-1C and used in determining residual lung volume.

Referring to FIG. 5, there is shown an exemplary container 500 (Container 110 in FIGS. 1B-1C), for holding exhaled air of the subject. The container may be a bag made from a flexible transparent plastic material and may be closed/sealed at one end and open at the other end with an axis 506 extending along the length of the bag from the closed end to the open end. Container 500 may be sealed using a tapered tube 508 that surrounds an outside of the container adjacent the open end, and a hollow mating portion 510. Mating portion 510 includes a mouth piece portion 512 and a round tube portion 514 extending away from the mouth piece portion 512. One end of the tube portion 514 opposite the mouth piece portion 512 is tapered and inserted into the container 500 to mate via the container 500 with tube 508 to form a seal 516. The subject exhales through the Mating portion 510 to fill the container 500.

When the bag is oriented in a vertical position, visible horizontal Markings 502A-502N (also referred to as demarcations) may be place at equal intervals in a row from the sealed end of the bag to the unsealed end around the axis 506. Sequential numerical numbers may be placed adjacent each of the markings 502a-502n indicating a distance from the marking to the sealed/closed end of the container 500.

When the subject exhales into an empty container while submerged in water, and the container is subsequently closed at the open end to cause the exhaled air and water in the container to substantially fill the container. The number adjacent the marking at the position just above the surface of the water in the container can be determined and used to calculate the volume of exhaled air. In one implementation this number will correspond to a distance in inches and/or centimeters from the closed end of the bag to the surface of the water in the bag. In another implementation the bag inflation pressure may be measured or estimated using a pressure sensor.

Figure 6A:
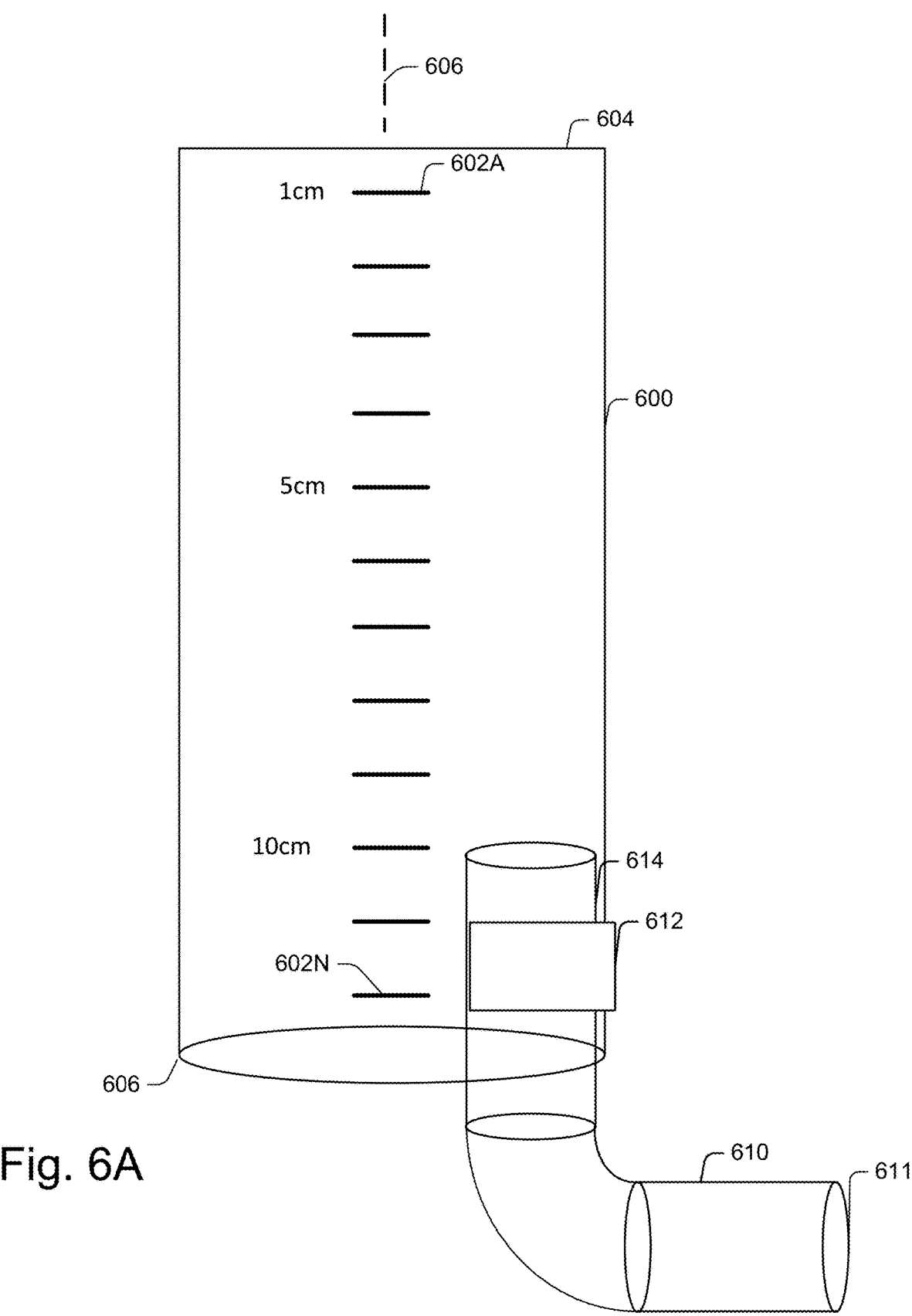
FIG. 6A is an isometric view and FIG. 6B is a top view of an alternate exemplary container with a snorkel replacing the mouth piece as shown in FIGS. 1B-1C and used in determining residual lung volume.
Figure 6B:
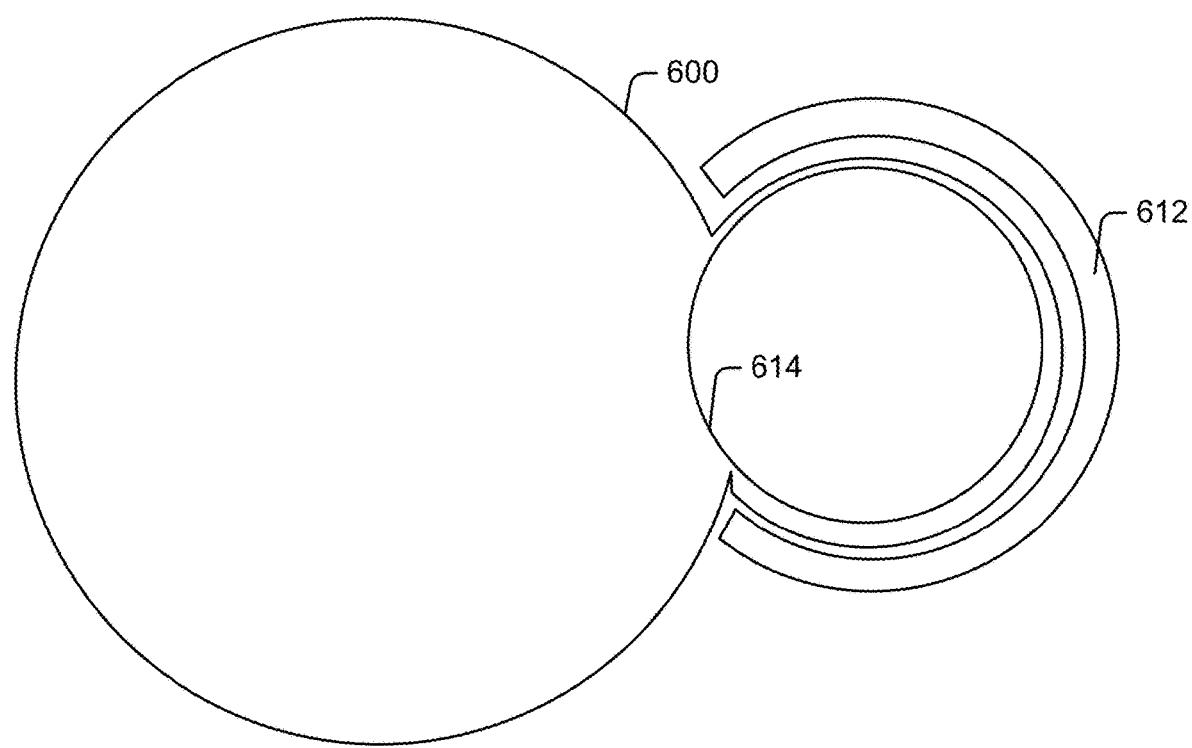

Referring to FIGS. 6A and 6B, there is shown an alternate version of container 600 (alternate version of container 500), for holding exhaled air of the subject. The container may be a bag made from a flexible transparent plastic material and may be closed/sealed at one end and open at the other end with an axis 606 extending along the length of the bag from the closed end to the open end.

When the bag is oriented in a vertical position, visible horizontal Markings 602A-602N (also referred to as demarcations) may be place at equal intervals in a row from the sealed end of the bag to the unsealed end around the axis 606. Sequential numerical numbers may be placed adjacent each of the markings 602a-602n indicating a distance from the marking to the sealed/closed end of the container 600.

Inserted into container 600 is a snorkel 610 having a breathing end 611 and an upper portion 614. Snorkel 610 may be a standard type snorkel having a mouthpiece (not shown) at one end and an opening at the snorkel's 611 other end. The open end of snorkel 610 is inserted into container 600. The subject exhales through snorkel 610 at depth D2 as described previously to at least partially fill the container 600. Referring to FIGS. 6A and 6B, a standard type clamp 612 may be placed on the outside of container 600 to engage with an upper portion 614 of snorkel 600 adjacent snorkel's open end. Clamp 612 holds snorkel 610 in place within container 600 while permitting water to escape through open end 606 of container 600 when the subject exhales via snorkel 610 into the container 600.

While the above detailed description has shown, described and identified several novel features of the invention as applied to a preferred embodiment, it will be understood that various omissions, substitutions and changes in the form and details of the described embodiments may be made by those skilled in the art without departing from the spirit of the invention. Accordingly, the scope of the invention should not be limited to the foregoing discussion but should be defined by the appended claims.

What is claimed is:

1. A method for determining with a lung volume computing device a residual lung volume in a body of a subject comprising:
   determining, with an air pressure measurement device, ambient air pressure;
   determining, with a water density measurement device, water density of water in a pool;
   submerging the subject in a pool of water at a first depth;
   completely exhaling air by the subject at the first depth;
   moving the subject to a shallower second depth;
   exhaling air, expanded in the body of the subject resulting from moving from the first depth to the second depth, into an air volume measuring device used to measure a volume of air exhaled by the subject as the body of the subject is submerged below the surface of the water at the second depth;
   receiving with the lung volume computing device a) the determined ambient air pressure from the air pressure measurement device, b) the determined water density measurement device water density of water in the pool, c) the first and second depth, and d) the volume of air exhaled by the subject as measured with the air volume measuring device; and
   determining, with the lung volume computing device, a residual lung volume (V1) of the subject based on the received a) determined ambient air pressure, b) the determined water density, c) the first and second depth, and d) the measured volume of air exhaled by the subject into the air volume measuring device (MVOA).

2. The method as recited in claim 1, wherein determining, with the lung volume computing device, a residual lung volume (V1) of the subject based on the received a) determined ambient air pressure, b) the determined water density, c) the first and second depth, and d) the measured volume of air exhaled by the subject into the air volume measuring device (MVOA) includes:
   determining V1 with the lung volume computing device using the formula V1=P2*MVOA/(P1−P2), where P1 is an underwater pressure determined based on the first depth and the water density, and P2 is an underwater pressure determined at the second depth based on the second depth and the water density.

3. The method as recited in claim 1 wherein determining with the water density measurement device water density of water in the pool includes the water density measurement device determining the water density by measuring a water temperature and a water purity.

4. An air volume measuring device to measure a residual lung volume in a body of a subject, the air volume measuring device comprising:
   a transparent expandable container with an open end and a closed end, the container having a length extending longer than a width;
   the container having a plurality of equally spaced radial demarcations extending from the closed end to the open end, at least one of the demarcations indicating a residual lung volume variable used to determine a measured volume of air exhaled by the subject when the subject exhales air expanded within the body, resulting from the subject moving from a deeper depth to a shallow depth in a pool of water after the subject empties air from the lungs of the subject into the pool at the deeper depth, into the container to expand walls of the container when an entire body of the subject is submerged below a surface of the pool of water at the shallow depth;

a lung volume electronic computing device to determine residual lung volume based on a reading of the at least one of the radial demarcations indicating the residual lung volume variable;

circuitry to receive a) a determined ambient air pressure from an air pressure measurement device, b) a determined water density from a measurement device operative to measure water density of water in the pool, c) a measurement corresponding to the shallow depth of the subject, d) a measurement corresponding to the deeper depth of the subject, and d) the residual lung volume variable of the subject; and circuitry to determine a residual lung volume (V1) of the subject based on the received a) determined ambient air pressure, b) the determined water density, c) the measurement of the shallow and the deeper depth, and d) measured volume of any potentially remaining air exhaled by the subject (MVOA) at the shallow depth after exhaling air by the subject at the deeper depth, wherein the circuitry to determine the residual lung volume (V1) of the subject uses the formula V1=P2*MVOA/(P1−P2), where P1 is an underwater pressure determined based on the deeper depth and the water density, and P2 is an underwater pressure determined at the shallow depth based on the measurement of the shallow depth and the determined water density.

5. The air volume measuring device of claim 4, further comprising:

a tube having an opening at a first end, and a mouthpiece at its other end, the tube operative to be inserted into the container at the first end to enable a mouth of the subject to contact the mouthpiece to exhale air via the tube into the container to expand walls of the container from a collapsed configuration to an expanded configuration.

6. The air measuring device of claim 5 further comprising:

a clamp to engage with an outside surface of the container to engage with the tube to hold the tube in place when the subject exhales air via the tube into the container.

7. The air volume measuring device of claim 4, wherein water from the pool enters the container to form a water level when the subject exhales air into the container, wherein the lung volume electronic computing device to determine residual lung volume by reading the at least one of the radial demarcations adjacent the water level, and wherein the at least one of the radial demarcations indicates air expanded within the body that resulted from the subject moving from a deeper depth to the shallow depth in the pool of water after the subject empties air from the lungs of the subject into the pool at the deeper depth.

8. A system for determining residual lung capacity of a subject, the system comprising:

an air pressure measurement device to determine ambient air pressure;

a water density measurement device to determine water density of water in a pool;

an air volume measuring device (AVMD) that includes a transparent bag with an open end and a closed end, the bag having a length extending longer than a width, the bag including:

a plurality of equally spaced radial demarcations imprinted on the bag and extending from the closed end to the open end around an axis extending through the length of the bag, a plurality of numbers adjacent the demarcations and printed on the bag, the numbers respectively corresponding to a lung volume used to determine a residual lung volume of the subject when the subject exhales air, expanded in the body of the subject as a result from moving from a first deeper depth (D1) to a second shallow depth (D2), into the bag when an entire body of the subject is submerged below a surface of the pool of water at depth D2 after the subject completely exhales air at depth D1 in the pool; and a lung volume computing device comprising:

circuitry to receive a) the determined ambient air pressure from the air pressure measurement device, b) the determined water density measurement device water density of water in the pool, c) a measurement corresponding to the first deeper depth D1 and second shallow depth D2, and d) a measured volume of air expanded in the body of the subject as a result from moving from depth D1 to depth D2 and exhaled by the subject at depth D2 as measured with the AVMD after exhaling air in the pool at depth D1; and circuitry to determine a residual lung volume (V1) of the subject based on the received a) determined ambient air pressure, b) the determined water density, c) the measurement corresponding to the depth D1 and the depth D2, and d) the measured volume of air expanded in the body of the subject as a result from moving from depth D1 to depth D2 and exhaled by the subject at depth D2 into the AVMD after exhaling air in the pool at depth D1, wherein the circuity to determine the residual lung volume (V1) of the subject uses the formula V1=P2*MVOA/(P1−P2), where P1 is an underwater pressure determined based on the deeper depth and the water density, and P2 is an underwater pressure determined at the shallow depth based on the measurement of the shallow depth and the determined water density.

9. The system as recited in claim 8, wherein the computing device further comprises a display to indicate the residual lung volume of the subject.

10. The system as recited in claim 8, further comprising a rope extending downward into a pool and connected to a float at one end, the rope having a plurality of markings with numbers adjacent thereto indicating a depth in the pool including depth D1 and D2, such that subject can observe the numbers markings and exhale at depth D1 and D2.

* * * * *